US012616388B2

(12) United States Patent
Shih

(10) Patent No.: US 12,616,388 B2
(45) Date of Patent: May 5, 2026

(54) CHINESE PULSE WAVE MEASURING DEVICE AND USE METHOD THEREOF

(71) Applicant: Ming-Cheng Shih, Hsinchu (TW)

(72) Inventor: Ming-Cheng Shih, Hsinchu (TW)

( * ) Notice: Subject to any disclaimer, the term of this patent is extended or adjusted under 35 U.S.C. 154(b) by 561 days.

(21) Appl. No.: 18/098,729

(22) Filed: Jan. 19, 2023

(65) Prior Publication Data

US 2023/0248253 A1 Aug. 10, 2023

Related U.S. Application Data

(60) Provisional application No. 63/304,367, filed on Jan. 28, 2022.

(51) Int. Cl.
*A61B 5/0255* (2006.01)
*A61B 5/00* (2006.01)
*A61B 5/024* (2006.01)

(52) U.S. Cl.
CPC ........ *A61B 5/0255* (2013.01); *A61B 5/02427* (2013.01); *A61B 5/7225* (2013.01)

(58) Field of Classification Search
CPC . A61B 5/0255; A61B 5/02427; A61B 5/7225; A61B 5/02422; A61B 5/6824; A61B 5/4854
See application file for complete search history.

(56) References Cited

U.S. PATENT DOCUMENTS

| | | | | |
|---|---|---|---|---|
| 2010/0076282 A1* | 3/2010 | Sandmore | ............ | A61B 5/6843 |
| | | | | 600/587 |
| 2013/0303923 A1* | 11/2013 | Lerner | ............... | A61B 5/02208 |
| | | | | 600/490 |
| 2015/0198797 A1* | 7/2015 | Andre | .................. | A61B 90/361 |
| | | | | 348/80 |
| 2016/0120420 A1* | 5/2016 | Liedl | .................. | A61B 17/1355 |
| | | | | 600/492 |

* cited by examiner

*Primary Examiner* — Abid A Mustansir

(57) ABSTRACT

A Chinese pulse wave measuring device is provided, which includes an airbag, a pressure control module, a displacement sensing module, a scanning position control module, and a computing device. The above-mentioned pressure control module, displacement sensing module, and scanning position control module are respectively communicationally connected to the computing device, and the pump of the pressure control module is connected to the airbag through gas tube and valve. A method of using the above-mentioned pulse wave measuring device is also provided.

14 Claims, 9 Drawing Sheets

1

CHINESE PULSE WAVE MEASURING DEVICE AND USE METHOD THEREOF

CROSS-REFERENCE TO RELATED APPLICATION

The present application claims priority from U.S. Provisional Patent Application No. 63/304,367 filed on Jan. 28, 2022, the contents of which are incorporated herein by reference in their entirety.

BACKGROUND

Technical Field

The disclosure relates to a physiological characteristic measurement system and its use method, especially related to a pulse wave measuring device and its use method.

Description of Related Art

At present, there are many different pulse diagnosis devices or instruments used to detect the physiological state of the people, and the current technology is almost all through the pressure film sensor. After a rough judgment of the pulse location by an operator, the pressure film sensor is aimed at one of the positions on the person's limbs, and with the help of an airbag and by adjusting the pressure of the airbag, the depth of the airbag pressing on the wrist is adjusted. Then, the pressure film sensor measures the dynamic pressure generated by the human body pulse and the static pressure of the depression depth to serve as a reference for the pulse signal and depression depth signal.

However, due to different operating habits of the operator, the static pressure of the depression depth and the depth of depression do not exhibit a linear relationship, resulting in measurement errors in physiological states. Therefore, it is necessary to develop a measuring system to measure the pulse wave of pulse diagnosis, in order to accurately measure various physiological state information of the subject being tested.

SUMMARY

In order to accurately measure various physiological state information of a subject, one aspect of the present invention is to provide a pulse wave measuring device and a method for using the same. The above-mentioned pulse wave measuring device is adapted to the wrist of the subject. The pulse wave measuring device is in contact with the test area of the subject's wrist, and the test area comprises the position of the subject's artery to detect the relevant physiological characteristic information of the pulse wave of the subject's artery, such as pulse characteristic wave.

BRIEF DESCRIPTION OF THE DRAWINGS

In order to further understand the techniques, means and effects of the present invention, reference may be made to the following detailed description and accompanying drawings, so that the purpose, features and concepts of the present invention may be thoroughly and specifically understood. However, the following detailed description and drawings are only for reference and illustration of the implementation of the present invention and are not intended to limit the present invention.

2

Figure 1:
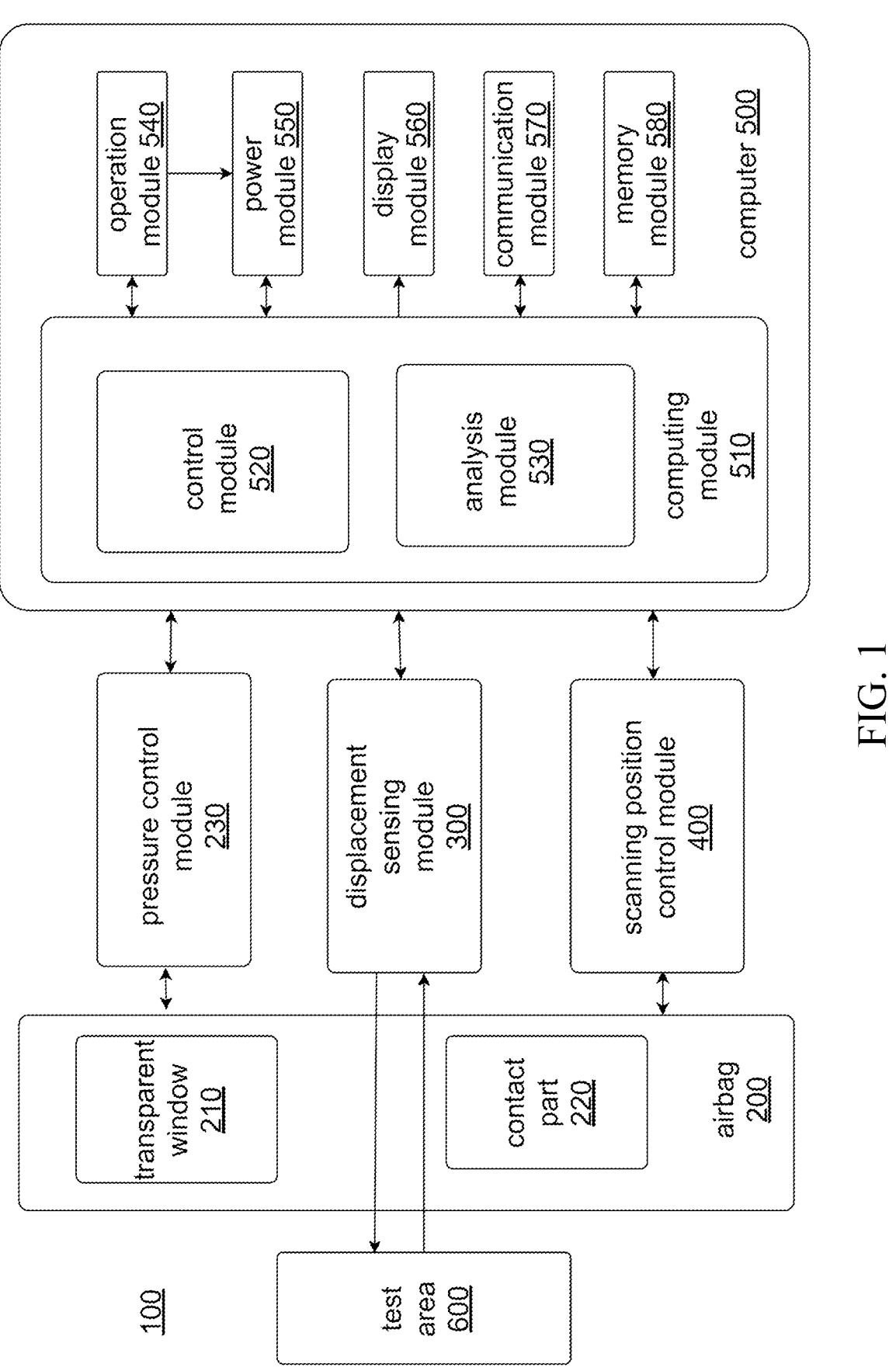

FIG. 1 is a functional block diagram of a pulse wave measuring device for pulse diagnosis according to an embodiment of the present invention.

Figure 2:
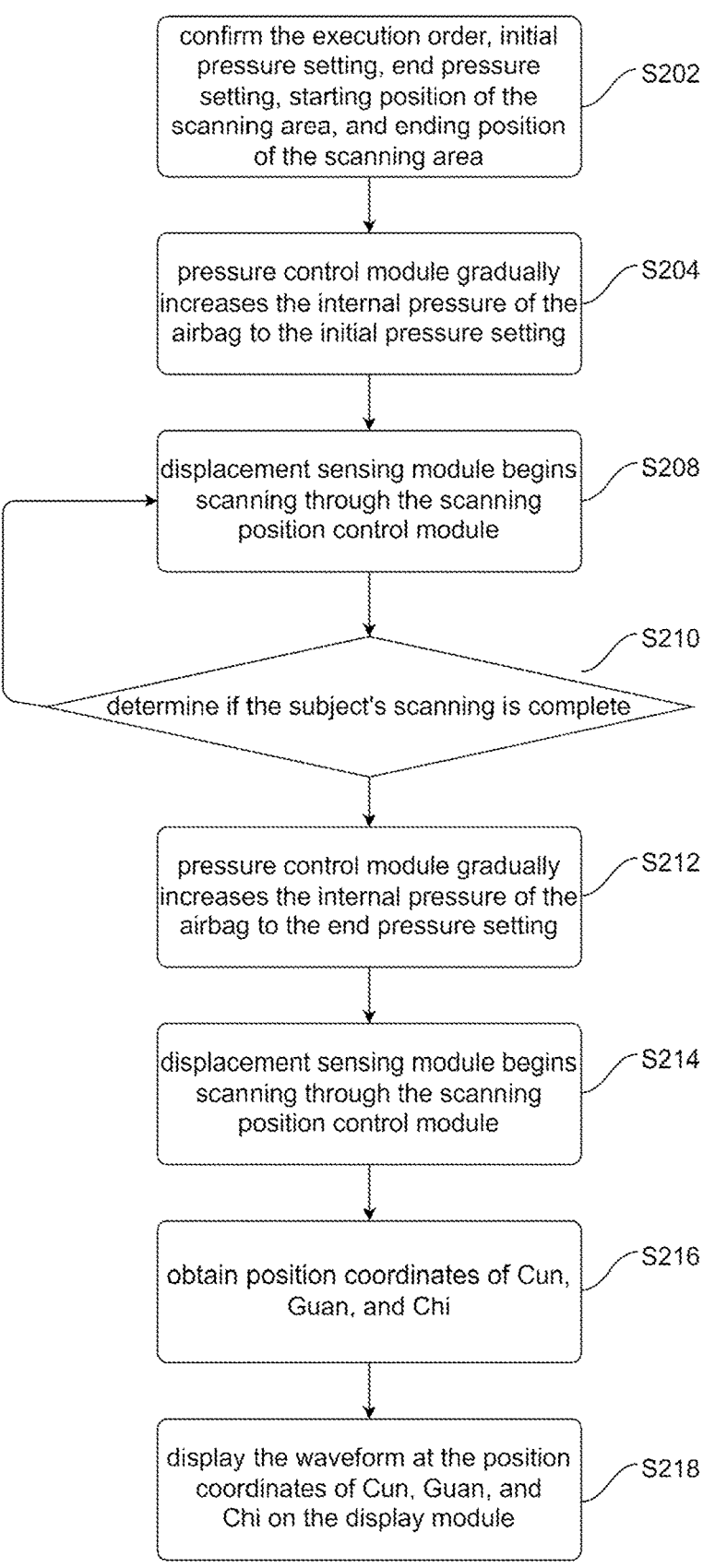

FIG. 2 is a flow chart illustrating a first stage of a pulse wave measurement method using the pulse wave measuring device shown in FIG. 1 according to an embodiment of the present invention.

Figure 3:
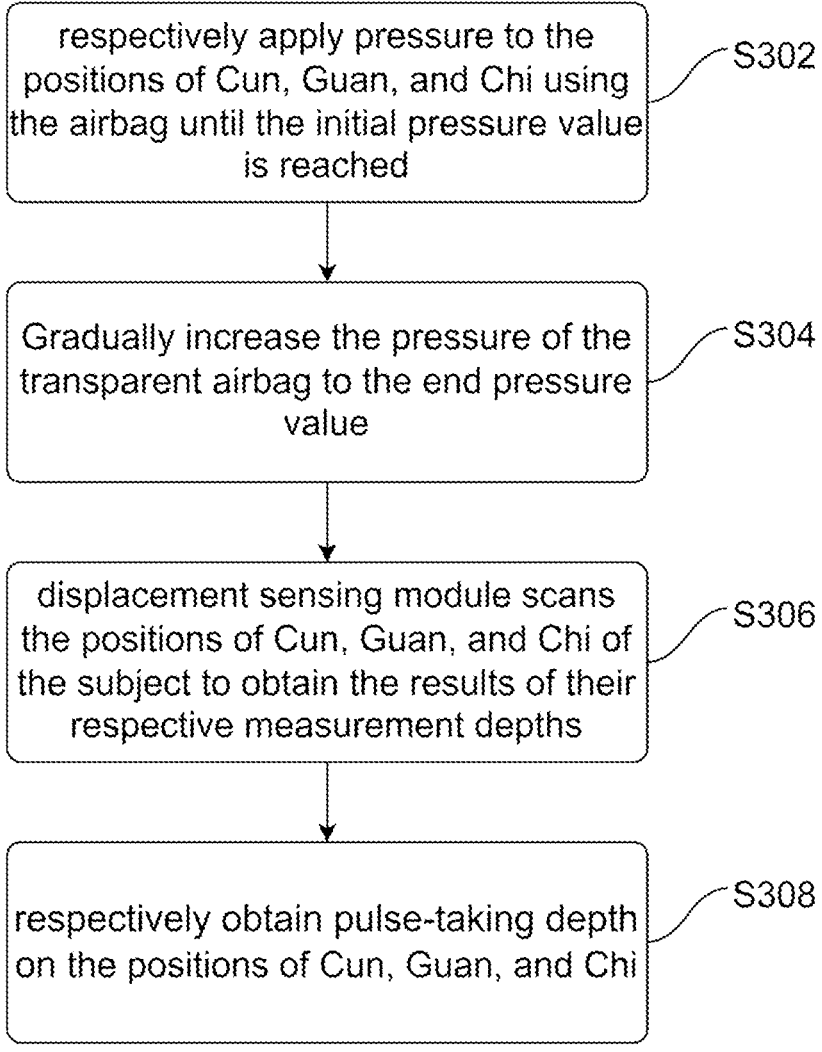

FIG. 3 is a flow chart illustrating a second stage of the pulse wave measurement method using the pulse wave measuring device shown in FIG. 1 according to an embodiment of the present invention.

Figure 4:
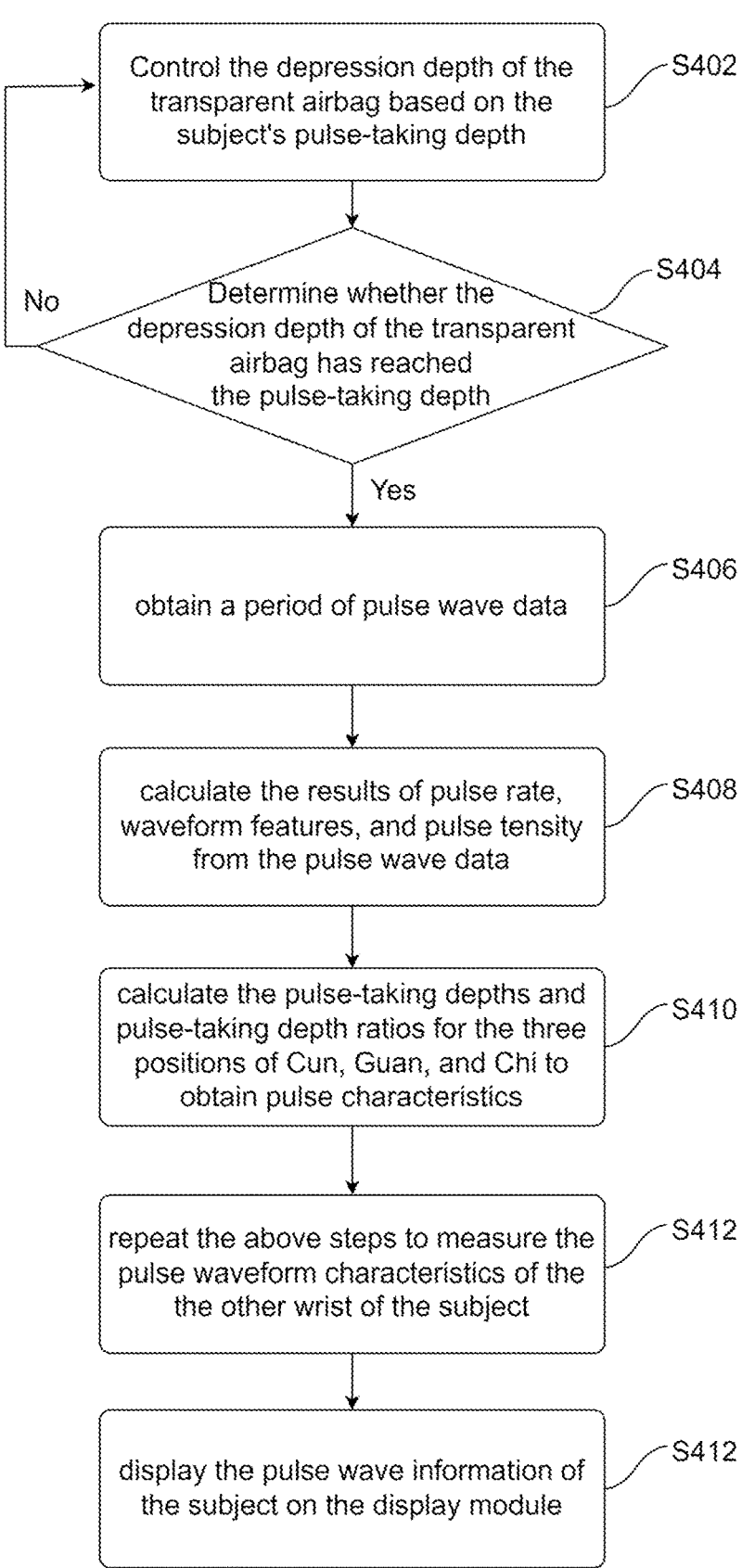

FIG. 4 is a flow chart showing a third stage of the pulse wave measuring method using the pulse wave measuring device shown in FIG. 1 according to an embodiment of the present invention.

Figure 5:
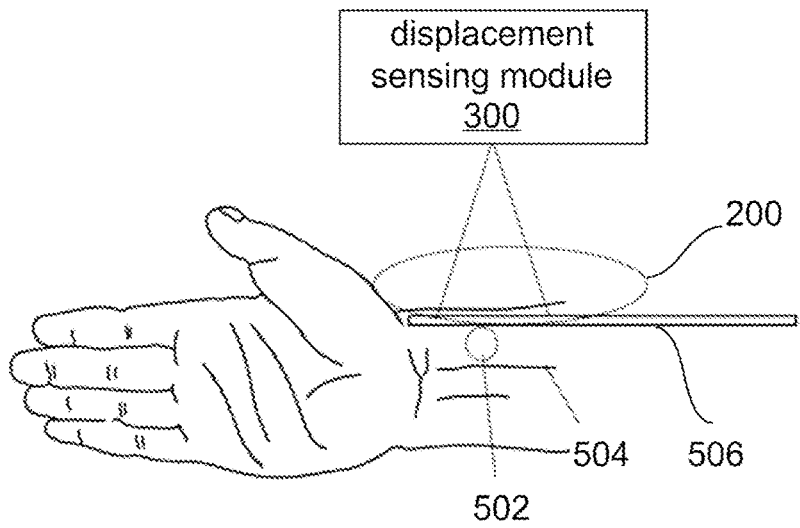

FIG. 5 is a schematic diagram showing the structure of the wrist and a schematic diagram of the system when using linear displacement sensor.

Figure 6:
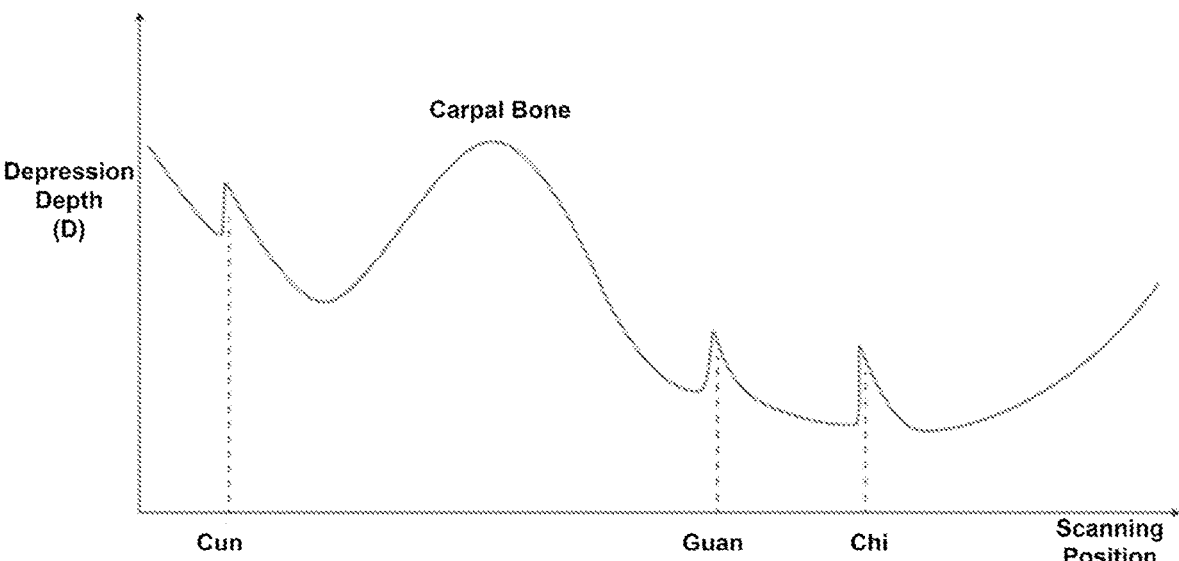

FIG. 6 is a schematic diagram showing the pulse wave at the Cun, Guan, and Chi pulse position measured by the linear laser displacement meter along the direction paralleling blood vessels according to an embodiment of the present invention.

Figure 7:
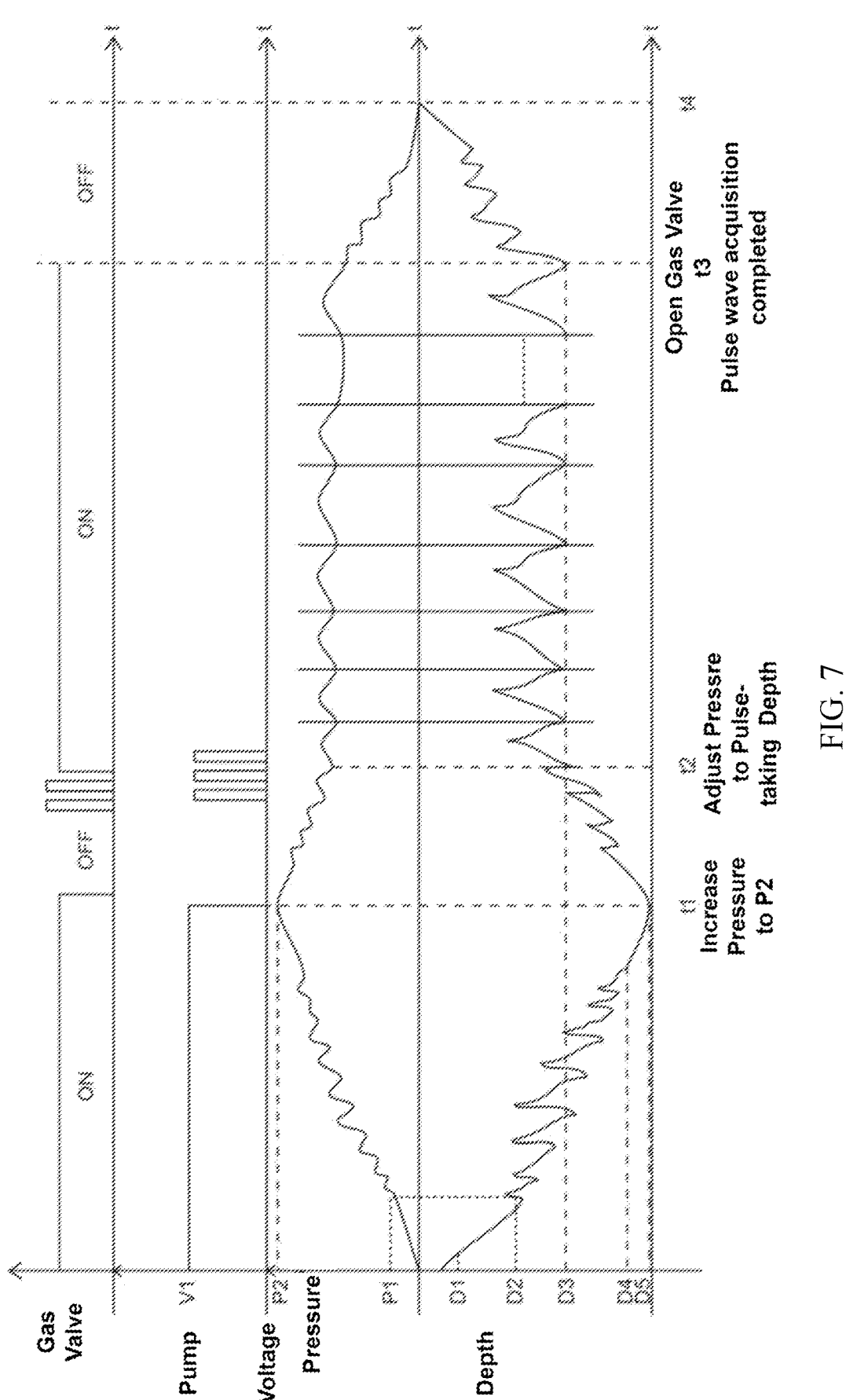

FIG. 7 is a schematic diagram showing the waveform of the pulse taking operation process and pulse characteristics obtained according to an embodiment of the present invention.

Figure 8:
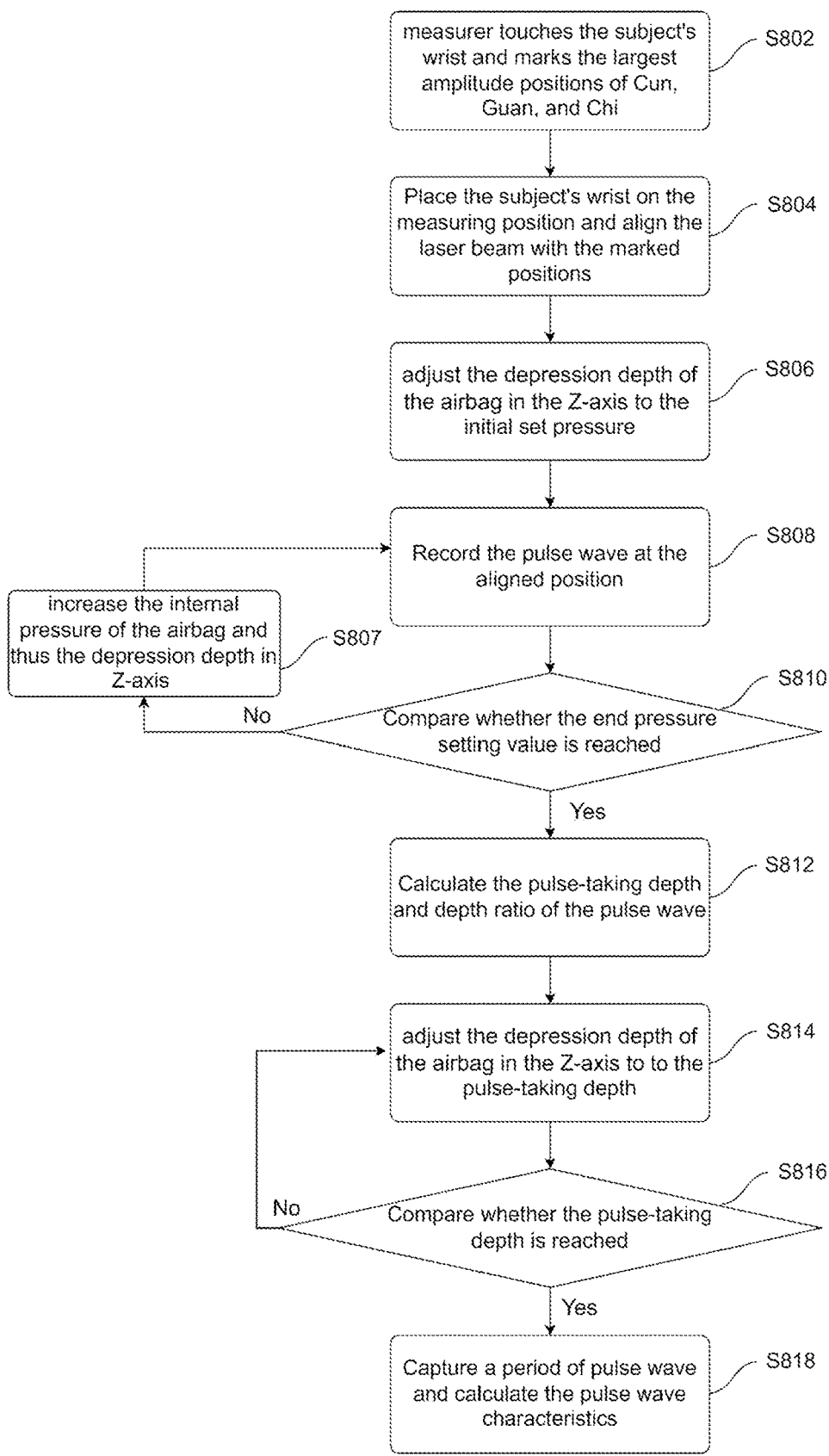

FIG. 8 is a flowchart illustrating a method of using the pulse wave measuring device shown in FIG. 1 according to an embodiment of the present invention, wherein the pulse wave measuring device 100 does not have a scanning position control module 400, and the displacement sensing module 300 is a point-type photoelectric displacement sensor.

Figure 9A:
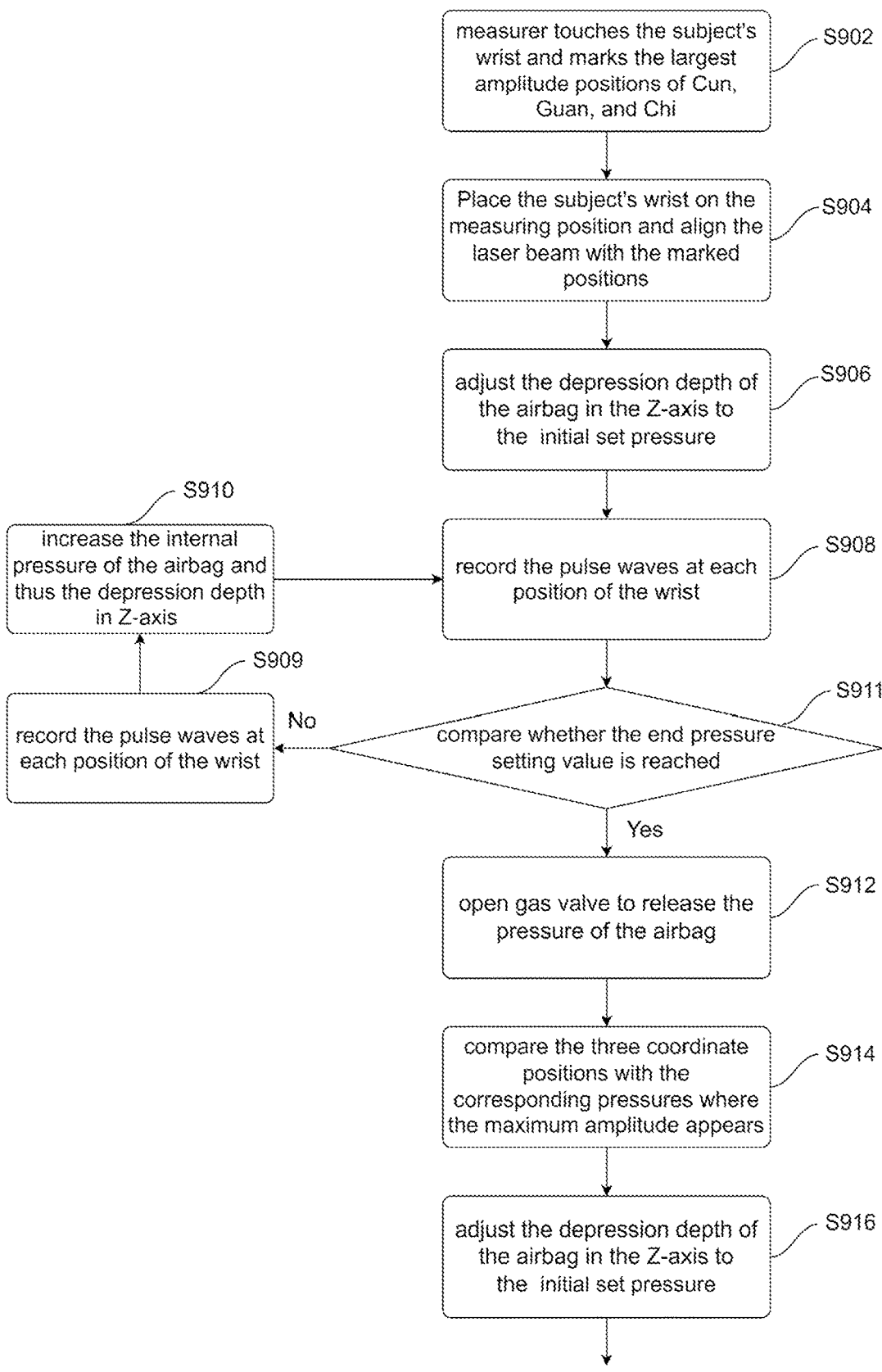
Figure 9B:
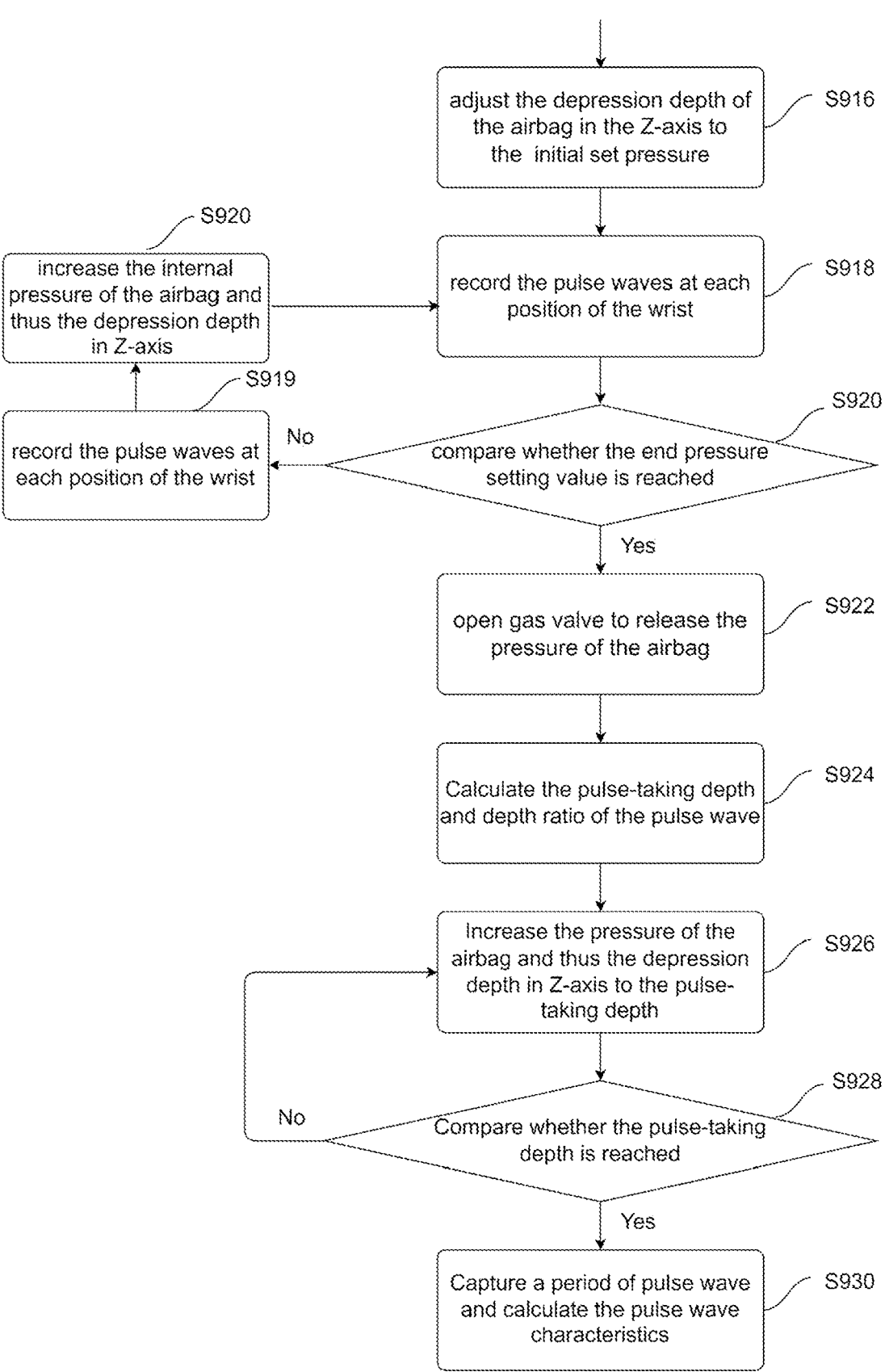

FIGS. 9A-9B are flowcharts illustrating a method of using the pulse wave measuring device shown in FIG. 1 according to another embodiment of the present invention, wherein the pulse wave measuring device 100 does not have the scanning position control module 400, and the displacement sensing module 300 is a linear or area-type photoelectric displacement sensor.

DETAILED DESCRIPTION

Definition: the XY plane is substantially parallel to the skin surface of a subject, wherein the X axis is substantially parallel to the direction of blood vessels of the subject, and the Y axis is substantially perpendicular to the direction of the blood vessels of the subject. Therefore, the Z axis is a direction substantially perpendicular to the skin surface of the subject. The definitions of the X-axis, Y-axis and Z-axis mentioned in the following description are the same as this.
Pulse Wave Measuring Device for Pulse Diagnosis Please refer to FIG. 1, which is a functional block diagram of a pulse wave measuring device for pulse diagnosis according to an embodiment of the present invention. In FIG. 1, the pulse wave measuring device 100 comprises an airbag 200, a pressure control module 230, a displacement sensing module 300, a scanning position control module 400 and a computer 500. The scanning position control module 400 is an optional component, that is, a component that may be omitted.

The airbag 200 comprises at least a transparent window 210 and a contact part 220. The material of the main body of the airbag 200 may be made from any available polymer material, such as (but not limited to) polymethyl methacrylate (PMMA), cellulose acetate (CA), nylon-66 polyamide resin (PA-66), nylon-6 polyamide resin (PA-6), polybuty-lene terephthalate (PBT), polyethylene terephthalate (PET), poly(phthalylene oxide) (PPO), polycarbonate (PC), ethylene-vinyl acetate copolymer (EVA), low-density polyethylene (LDPE), high-density polyethylene (HDPE), polypropylene (PP), polyvinyl chloride (PVC), polyoxymethylene (POM) or polyurethane (PU).

The above-mentioned transparent window 210 is used for aligning the displacement sensing module 300, so it may be made from a high-hardness transparent material, such as but not limited to glass, quartz, polystyrene (PS) or acrylonitrile-butadiene-styrene copolymer (ABS). The surface of the transparent window 210 may also be coated with an anti-reflection film to increase light penetration, reduce reflected light clutter and increase abrasion resistance.

The above-mentioned contact part 220 is used to contact the skin of the test subject's test area 600, so the contact part 220 may be made from a flexible (with a hardness range of Shore hardness 20C to 72D) and elastic polymer material to facilitate a close adhesion to the skin of the test subject's test area 600. The above-mentioned polymer materials may be, for example, thermoplastic elastomers (TPE). The available thermoplastic elastomers may be, for example, TPU (thermoplastic polyurethane), TPO (polyolefin elastomer), TPV (dynamically vulcanized polyolefin elastomer), TPS/TPR (thermoplastic styrene/thermoplastic rubber), TPEE (thermoplastic polyester elastomer), or TPA (polyamide elastomer). The inner surface of the above-mentioned contact part 220 facing the airbag is smooth or may be coated with a layer of reflective material to enhance light reflection to facilitate uniform reflection (rather than scattering) of light.

The pressure control module 230 controls the internal pressure of the airbag 200 by inflating or depressurizing the inside of the airbag 200. According to some embodiments, the pressure control module 230 may comprise, for example, a pressure sensor, a pump, a gas tube, and a gas valve. The pressure sensor may sense the internal pressure of the airbag 200, and the two ends of the gas tube are respectively connected with the pump and the airbag 200, and a suitable gas valve is installed at a suitable position of the gas tube. Therefore, the integration of the operation (forward and reverse rotation) of the motor in the pump and the air valve may be relied on to control the gas inflow into or outflow from the airbag 200, thereby controlling the internal pressure of the airbag 200. This allows for the control of the depression depth of the skin of the test area 600 of the test subject in the Z-axis by the airbag 200.

The above-mentioned displacement sensing module 300 is used to measure the distance in the Z-axis direction between the displacement sensing module 300 and the skin of the test area 600 of the test subject (when the contact part 220 of the airbag 200 is made of transparent material) or measure the distance in the Z-axis direction between the displacement sensing module 300 and the contact part 220 of the airbag 200 (when the contact part 220 of the airbag 200 is made of opaque material).

The displacement sensing module 300 may be any available displacement sensor, with a minimum measuring resolution of 50 μm. For example, displacement sensors with resolutions of 50 μm, 40 μm, 30 μm, 20 μm, 10 μm, or 1 μm may be used. The displacement sensor mentioned above may be, for example, a photoelectric displacement sensor that uses various light sources to measure distance. The photoelectric displacement sensor mentioned above may be a laser displacement meter, a fiber-optic displacement sensor, a three-dimensional scanner (3D scanner, such as a binocular depth CCD plus a programmable Structured light system), Time of Flight (TOF for short) device, or distance measuring device of laser interferometer, for example. If classified according to the shape of the detectable area of the displacement sensing module 300, the above displacement sensing module 300 may be a point-type, linear-type, or area-type displacement sensor.

As mentioned above, when the displacement sensing module 300 is a photoelectric displacement sensor, since the displacement sensing module 300 is adjacent to the transparent window 210 of the airbag 200, the light emitted by the light source of the displacement sensing module 300 may penetrate the transparent window 210 of the airbag 200.

When the contact part 220 of the airbag 200 is made from a transparent material, the light emitted by the light source of the displacement sensing module 300 will directly irradiate on the skin of the test area 600 of the subject, and then reflect back to the receiver of the displacement sensing module 300, enabling the displacement sensing module 300 to measure the distance between the displacement sensing module 300 and the skin of the test area 600 of the subject.

When the contact part 220 of the airbag 200 is made from an opaque material, the light emitted by the light source of the displacement sensing module 300 will directly irradiate on the inner surface of the contact part 220 of the airbag 200 facing the airbag, and then reflect back to the receiver of the displacement sensing module 300, enabling the displacement sensing module 300 to measure the distance between the displacement sensing module 300 and the contact part 220 of the airbag 200. Therefore, when the inner surface of the contact part 220 facing the airbag 200 is smooth enough or coated with a layer of reflective film, the degree of scattering after light reflection may be effectively reduced, allowing the receiver of the displacement sensing module 300 to receive signals with a better signal-to-noise ratio (S/N ratio) and make the distance measurement of the displacement sensing module 300 more accurate.

In addition, it is worth mentioning that the displacement sensing module 300 may further comprise a filter. Since the original displacement signal obtained by the displacement sensing module 300 contains the displacement value of the AC signal of the pulse wave, the AC signal of the pulse wave may be filtered out through the filter, and the remaining stable DC signal represents the Z-axis Depth displacement value. If the displacement sensing module 300 does not comprise a filter, that is, the AC signal of pulse wave is also comprised, the measured value obtained is a dynamic pulse wave signal. In addition, the so-called displacement signal refers to the difference obtained by subtracting the second position from the first position, wherein the first position is obtained when the airbag 200 is not pressurized (or lightly pressed) and touches the test area 600 of the subject, and the second position is obtained when the airbag 200 is pressurized (or heavily pressed) and touches the test area 600 of the subject. Please refer to the relevant description of the pulse wave measurement method described later.

The aforementioned scanning position control module 400 is used to control the displacement sensing module 300 to move onto the test area 600 of the subject and to control the displacement sensing module 300 to perform distance measurement scanning within the range of the test area 600. For example, when measuring the pulse wave of the subject's radial artery, the subject's pulse wave may vary at any time, which changes the "pulse measurement distance" from the displacement sensing module 300 to the skin of the test area 600 of the subject or to the contact portion 220 of the airbag 200. Therefore, the scanning position control module 400 can be used to control the displacement sensing module

300 to move to above the body surface of the test area 600 of the subject's radial artery and perform measurement of the changing "pulse measurement distance" over time and distance-measurement scanning in the test area 600.

The scanning position control module 400 is an optional component, that is, a component that may be omitted. When there is no scanning position control module 400, the user may directly move the displacement sensing module 300 to the test area 600 of the test subject and let the displacement sensing module 300 scan the test area 600 of the test subject. The displacement sensing module 300 may be a photoelectric displacement sensor whose detection area is a point, liner, or area type.

According to some other embodiments, the scanning position control module 400 may comprise an X-Y dual-axis position controller (such as X-Y dual-axis moving platform or cylindrical coordinate moving mechanism) and a point-type photoelectric displacement sensor module 300 that can be combined to perform distance scanning of the test area 600 of the test subject.

The above-mentioned computer 500 is respectively connected to the above-mentioned pressure control module 230, displacement sensing module 300, and scanning position control module 400 to respectively send control signals to the pressure control module 230, displacement sensing module 300, and scanning position control module 400, or receive information transmitted by the pressure control module 230, displacement sensing module 300, and scanning position control module 400. The computer 500 can be any computing device with sufficient computing capability, such as various types of computers, microprocessors, or mobile computing devices.

According to some embodiments, the computer 500 comprises a computing module 510, an operating module 540, a power module 550, a display module 570 and a memory module 580.

The above computing module 510 may comprise a computing module 5100 and an analyzing module 530. The computing module 5100 is responsible for providing control instructions for the pressure control module 230, the displacement sensing module 300, and the scanning position control module 400. The analysis module 530 is responsible for calculating and analyzing the information transmitted from the pressure control module 230, the displacement sensing module 300, and the scanning position control module 400.

The above-mentioned operation module 540 provides a user interface, allowing the user to issue a control instruction through the operation module 540 to control the operation of the pressure control module 230, the displacement sensing module 300 and the scanning position control module 400.

The power supply module 550 is used to supply the power required by the computer 500. The power module 550 may be an AC power source (for example, the power of a power plant may be obtained through a general power socket) or a DC power source (for example, various dry batteries or rechargeable storage batteries).

The display module 560 is used to display the user interface of the computing module 5100, the information transmitted from the pressure control module 230, the displacement sensing module 300, and the scanning position control module 400 to the analysis module 530, as well as the results of the information analyzed by the analysis module 530.

The communication module 570 is used to communicate with the pressure control module 230, the displacement sensing module 300, the scanning position control module

400, and some external databases. The aforementioned external database may be, for example (but not limited to), a pulse condition comparison database, a Chinese herbal medicine database, or a combination thereof.

The above-mentioned memory module 580 may be any available volatile or non-volatile data storage device to store any data generated during the measurement process of the displacement sensing module 300.

From the above, it may be seen that the collaboration between the airbag 200 and the pressure control module 230, as mentioned above, can allow the airbag 200 to provide the depression depth on the Z-axis, allowing the displacement sensing module 300 to locate the optimal pulse wave measurement position on the Z-axis in terms of signal-to-noise ratio. The scanning position sensing module 400 allows the displacement sensing module 300 to find the pulse wave measurement position with the best signal-to-noise ratio on the XY plane. Therefore, the above-mentioned pulse wave measuring device 100 may easily find the optimal position for measuring pulse waves with the highest signal-to-noise ratio for radial displacement of the pulse wave of blood vessels in the test area 600 of the test subject. This improves the strength of the displacement signal of the original pulse wave, which can then be measured using a displacement sensor with high-precision and high-linearity. This may provide more detailed information about the pulse wave of the test subject, which is required for traditional Chinese pulse diagnosis.

Measurement Method of Pulse Wave:

Taking the Pulse Diagnosis of Traditional Chinese Medicine as Example

In order to describe in more detail how the pulse wave measuring device obtains the pulse wave characteristic wave of the test subject, the following describes the pulse wave measuring method using the pulse wave measuring device shown in FIG. 1. Please refer to FIG. 1 to FIG. 4, wherein FIG. 2 is a flow chart illustrating a first stage of a pulse wave measurement method using the pulse wave measuring device shown in FIG. 1 according to an embodiment of the present invention; FIG. 3 is a flow chart illustrating a second stage of the pulse wave measurement method using the pulse wave measuring device shown in FIG. 1 according to an embodiment of the present invention; FIG. 4 is a flow chart showing a third stage of the pulse wave measuring method using the pulse wave measuring device shown in FIG. 1 according to an embodiment of the present invention.

The pulse wave measurement method using the pulse wave measuring device 100 shown in FIG. 1 can be mainly divided into three stages. The first stage is to confirm the positions of Cun, Guan, and Chi pulses of the subject's wrist. The second stage is to apply pressure to the pulse-taking positions and calculate the pulse-taking depths of the Cun, Guan, and Chi pulses after confirming the pulse positions of Cun, Guan, and Chi pulses of the subject's wrist. The third stage is to measure the pulse waves and obtain the waveforms as well as pulse tensity and trend of the Cun, Guan, and Chi pulses. The measurement methods for each of the three stages will be explained below.

First Stage: Confirm Positions of Cun, Guan, and Chi Pulses on Subject's Wrist

In FIG. 2, to confirm the position and size of the scanning area of the test area 600 of the subject, two conditions of light pressure and heavy pressure are provided on the airbag 200 in the test area 600. In step S602, according to the pulse diagnosis program in the computing module 510, the execution order, initial pressure setting value, end pressure setting value, starting position of the scanning area and ending position of the scanning area are determined. The initial pressure setting value refers to the pressure value when the airbag 200 lightly presses the skin. The end pressure setting value refers to the pressure value when the airbag 200 heavily presses the skin, and the end pressure setting value is the pressure value that remains almost unchanged after the airbag 200 has been pressed to the depth of the hand bone. In addition, the initial position of the scanning area and the end position of the scanning area refer to the record initial and end positions of the scanning position control module 400.

As shown in FIG. 2, firstly, in order to confirm the scanning area of the test area 600 of the test subject, the airbag 200 is provided under two conditions of light pressure and heavy pressure in the scanning area. In step S202, according to the pulse diagnosis program in the computing module 510, the execution order, initial pressure setting value, end pressure setting value, starting position of the scanning area and ending position of the scanning area are determined. The initial pressure setting value refers to the pressure value when the airbag 200 lightly presses the skin. The end pressure setting value refers to the pressure value when the airbag 200 heavily presses the skin, and the end pressure setting value is the pressure value that remains almost unchanged after the airbag 200 has been pressed to the depth of the hand bone. In addition, the initial position of the scanning area and the end position of the scanning area refer to the record initial and end positions of the scanning position control module 400.

In step S204, the pressure control module 230 receives the measurement instruction, i.e., an instruction to measure the pulse wave. The pressure control module 230 issues a pressure control instruction to open the gas valve of the airbag 200, allowing air to enter the airbag 200 to gradually increase the pressure of the airbag 200 to the initial pressure setting value. An analog-to-digital converter can be used to return the pressure applied by the airbag 200 to the skin of the subject (initial pressure setting value) to the pressure control module 230.

In step S208, the control module 520 transfers a displacement sensing instruction and requests the displacement sensing module 300 to start scanning the scanning area of the wrist according to the set values of the scanning area start position and the scanning area end position.

Next, in step S208, while the scanning position control module 400 moves the displacement sensing module 300, the displacement sensing module 300 simultaneously or sequentially reads the values of the obtained displacement signals until the scanning operation of the set values of the start and end positions of the scanning area is completed. The scanning position control module 400 and the displacement sensing module 300 respectively transmit the coordinates and depths (referred to as the initial scan area coordinates) of each measurement point in the scanning area to the memory module 580 of the computer 500.

In step S210, it is determined whether the start and end positions of the scanning area are scanned. If the scanning of the wrist's scanning area has not been completed, return to step S208. The displacement sensing module 300 continue to scan between the start position of the scanning area and the end position of the scanning area until all scanning areas are completed. If the scanning is completed, go to step S212.

In step S212, the pressure control module 230 requests the pressure in the airbag 200 to reach the end pressure setting value (heavy pressure) through the pressure control instruction. This step is to scan the radial artery area of the wrist to first determine the position of the carpal bone and the radial artery. Similarly, during the heavy pressure phase, the displacement signals of all scanning areas, i.e., the coordinates and measured depths of each measurement point in the scanning area of the wrist, are obtained through the displacement sensing module 300, which represents the maximum depth range scanned.

Then, in step S214, under the situations of light pressure (initial pressure setting value) and heavy pressure (terminating pressure setting value) by the pressure control module 230, the initial position of the same point coordinate is set by the displacement sensing module 300. The displacement amount of the coordinate depth of the scanning area is subtracted from the displacement amount of the coordinate depth of the end scanning area to obtain the change amount of the measured distance from the skin to the displacement sensing module 300 measured at the same coordinate point.

Please refer to FIG. 5 at the same time. FIG. 5 is a schematic diagram showing the tissues of various parts of the wrist and a schematic diagram of the system when linear displacement meter is used.

In step S216, due to the hard tissue near the radial artery (i.e., the carpal bone 502 and the flexor carpi radialis tendon 504 in FIG. 5), the depth change was the smallest during the two compressions of the airbag 200. Conversely, the soft tissue (i.e., the radial artery 506 and its surrounding area in FIG. 5) had the largest depth change. Thus, the relative positions of the carpal bones, metacarpals, and flexor carpi radialis tendon were determined based on the location of the area with a small depth change, while the distribution area of the radial artery was determined based on the area with a large depth change. Then, within the location surrounded by the radius and the flexor carpi radialis tendon 504, the area where the pulse beat was detected inside the position surrounded by the carpal bone and flexor carpi radialis tendon was identified as the position of the radial artery.

Next, the point of pulse wave with maximum amplitude along the position of the radial artery is identified, and its coordinates are the location of "Cun." Finally, in the vascular area where the wrist bone and the flexor carpi radialis muscle tendon surround, the two points with strongest pulse wave are found. The position closer to the carpal bone is labeled as the coordinate of "Guan" and the position further away from the carpal bone is labeled as the coordinate of "Chi." Referring to FIG. 5, a schematic diagram of the pulse wave at the positions of Cun, Guan, and Chi measured by a linear laser displacement sensor along the direction parallel to the blood vessel can be obtained, as shown in FIG. 6.

Finally, in step S218, after the above steps are completed, the control module 520 may display the waveform shown in FIG. 7 on the display module 560 through the display module 560. FIG. 7 is a schematic diagram showing the waveform of the pulse-taking operation process and pulse characteristics obtained according to an embodiment of the present invention.

Second Stage: Pressurize the Pulse Taking Position of Cun, Guan, and Chi Respectively to Calculate the Pulse Taking Depth of Cun, Guan, and Chi After finding the Cun, Guan, and Chi position on the wrist of the test subject in the first stage, it is necessary to determine at what depth the clearest pulse signal can be obtained from the test subject.

In step S302 of FIG. 3, similar to the first stage, the pressure control module 230 allows the pressure inside the airbag 200 to reach the initial pressure setting value at the measurement points of the Cun, Guan, and Chi.

Next, in step S304, the pressure control module 230 controls the gas valve to inflate the airbag 200 and gradually increase the pressure to the end pressure setting value. Then, under the pressure that may stabilize the airbag 200, adjust the precise amount of downward pressure to obtain a stable pulse acquisition depth, so that the displacement sensing module 300 has enough time to acquire the pulse signal, and acquire the pulse signal with the highest signal-to-noise ratio, which is beneficial to the identification and processing of subsequent waveform signals. Next, the pressure control module 230 returns the pressure reading to the memory module 580 of the computer 500 or stores the pressure reading in an external data storage device of the computer 500 through the communication module 570. It is worth noting that the initial displacement value is zero when the airbag 200 touches the skin, and the displacement value is negative when the airbag 200 continues to press down (after applying heavy pressure), and relative distance is used as the basis for calculating proportions between different individuals.

Then in step S306, the scanning position control module 400 of the displacement sensing module 300 scans the position of the subject's Cun, Guan, and Chi, and the displacement sensing module 300 calculates the read values of the displacement signal from no pressure to heavy pressure, and compute the cartesian coordinates or cylindrical coordinates of the Cun, Guan, and Chi positions, so that the position coordinates of different points in the scanning area may be integrated with the results of the depth measurement. Among them, the displacement signal readings simultaneously mix the displacement values of the depths and the pulse waveforms. Therefore, the displacement values of the depth may be obtained by obtaining a stable DC signal through the filter. If the AC signal of the pulse wave is not filtered out, the measured value will be a dynamic pulse waveform signal. The depth value of the maximum amplitude of the pulse wave signal is calculated.

Next, in step S308, through the operation of the pulse diagnosis program, the pulse-taking depths at the positions of Cun, Guan, and Chi are obtained. The depths of the positions where the pulse waves with the largest amplitude are the pulse-taking depths.

Third Stage: Respectively Measuring Pulse Wave to Obtain Waveforms as Well as Pulse Tensity and Trend of Pulse Waves at Positions of Cun, Guan, and Chi In FIG. 4, in step S402, the pressure control module 230 controls the depression depth of the airbag 200 according to the pulse-taking depth at the Cun, Guan, and Chi positions of the subject as the initially set pulse-taking depth at Cun, Guan, and Chi.

Next, in step S404, it is judged whether the depression depth of the airbag 200 has reached the pulse-taking depth, wherein the pressure inside the airbag 200 may be adjusted by the pressure control module 230 to obtain an accurate pulse-taking depth. If not, return to step S402, and the pressure control module 230 continues to control to increase the pressure of the airbag 200. If yes, then in step S406, when the pressure control module 230 detects that the airbag 200 has reached the pulse-taking depth, the displacement sensing module 300 takes the position coordinates of the subject's Cun, Guan, and Chi as the initial set position coordinates of the subject's Cun, Guan, and Chi. Pulse wave data for a period of time (for example, 1 minute) is captured, and store the wave data in the computer 500.

Next, in step S408, according to the pulse wave data obtained in step S406, the analysis module 530 calculates the pulse rate, pulse waveform, and pulse wave amplitude, and stores them in the computer 500 or an external data storage device of the computer 500.

Afterwards, in step S410, the analysis module 530 reads the pulse wave measurement result data, and then calculates the three positions of Cun, Guan, and Chi shown in FIG. 6, as well as the pulse-taking depth and the ratio of the pulse-taking depth shown in FIG. 7.

FIG. 7 is a schematic diagram showing the waveform of the pulse taking operation process and pulse characteristics obtained according to an embodiment of the present invention. In FIG. 7, pulse characteristics, such as pulse rate, pulse waveform feature, or/and pulse wave trend, are obtained through the pulse wave measurement result data.

Further, in FIG. 7, the depth at which the displacement sensing module 300 touches the skin of the test area 600 is D1, the depth at which the pulse waveform signal begins to appear is D2, and the depth at which the pulse waveform signal is maximum is D3, and the depth at which the pulse waveform signal begins to disappear is D4, and the depth at which the pressure reading value of the end pressure storage part is reached is D5. At this point, the overall depth is D5 minus D1 (D5–D1). Moreover, the depth ratio at which the pulse waveform signal begins to appear is (D1–D2)/(D5–D1), the depth ratio at which the pulse waveform signal begins to disappear is (D1–D4)/(D5–D1), and the depth ratio at which the pulse waveform signal begins to appear is (D2–D4)/(D5–D1), and the depth ratio at which the maximum pulse amplitude is obtained is (D1–D3)/(D5–D1).

When calculating the result of the pulse rate, a digital filtering process may be performed first to filter out low-frequency noise caused by respiration. Then, the lower limit value for calculating the peak is set. Finally, the number of pulse waveform within a period (for example, 1 minute) is calculated by the analysis module 530, i.e., the result shown in FIG. 7, and stored in computer 500 or external data storage device of the computer 500.

When calculating the pulse waveform features, the low-frequency noise caused by respiration is also filtered out first, and then the Fast Fourier transform (FFT) spectrum analysis is performed on the waveform captured from the time domain to decompose the waveform into a quantified analysis of the composition of different frequency waves. Finally, the results of the pulse wave spectrum analysis are stored in the computer 500 or external data storage device of the computer 500.

In addition, in step S412, the above-mentioned steps are repeated to measure the pulse waveform tensity of the other wrist of the subject and store them in the subject's data storage database. In step S414, after completing the measurements of both hands, the control module 520 can display the subject's pulse waveform on the display module 560, such as the waveform shown in FIG. 7, without limitation. Pulse Wave Measurement Method 1: Remove the Scanning Position Control Module and Use Point-Type Photoelectric Displacement Sensor The following refers to the situation where the scanning position control module 400 is removed from the system structure diagram, and the displacement sensing module 300 may be a point-type photoelectric displacement sensor. In this case, the displacement sensing module 300 may be manually operated to be moved onto the test area 600 of the subject for measurement.

Please refer to FIG. 1 and FIG. 8 at the same time. FIG. 8 is a flowchart illustrating a method of using the pulse wave measuring device shown in FIG. 1 according to an embodiment of the present invention, wherein the pulse wave measuring device 100 does not have the scanning position control module 400, and the displacement sensing module 300 is a point-type, liner-type or area-type photoelectric displacement sensor. In the following, the radial artery of the wrist of the subject is taken as the test area 600 as an example for illustration.

Enter the aforementioned first stage of measurement. In FIG. 8, in step S802, the measurer touches the wrist of the subject, and marks the place with the largest amplitude on the radial artery of the wrist as the test area 600 of the subject. In step S804, the point-type photoelectric displacement sensor is placed on the test area 600 at the radial artery of the wrist of the subject for measurement.

Then, enter the second stage of measurement. In step S806, the pressure control module 230 regulates the internal pressure of the airbag 200 to press the skin of the test subject in the Z-axis direction and adjusts to the initial pressure setting value (light pressure). In step S808, the radial displacement of the pulse wave of the blood vessel at the aligned position is recorded.

In step 810, whether the end pressure set value is reached is checked.

If not, go to step S807, where the pressure control module 230 continues to increase the pressure to regulate the depression depth of the airbag 200 in the Z-axis direction. Then in step S808, the displacement changes of the skin at the test area 600 of the subject due to the radial pulse waves of blood vessels are continuously recorded.

If yes, then enter step S812. Based on the recorded change curve of the skin displacement of the test subject at the test area 600 (the recording change curve will be referred to as recording the pulse wave for short later), the pulse-taking depth and the ratio of the pulse-taking depth relative to the thickness of the test subject's wrist can be calculated.

Enter the third stage. Then, enter step S814, the depression depth of the airbag 200 on the Z-axis is adjusted to the pulse-taking depth. In step S816, whether the airbag 200 is pressed down to the pulse-taking depth is compared. If not, then return to step S814 and adjust the depression depth of the airbag 200 on the Z-axis until the pulse-taking depth is reached. If yes, proceed to step S818, the waveform of the pulse wave recorded for a period of time (for example, 1 minute) is extracted, and the waveform features of the pulse wave is calculated.

Pulse Wave Measurement Method 2: Use Point-Type Photoelectric Displacement Sensor and Use Linear or Surface-Type Photoelectric Displacement Sensor The operation process of the linear-type photoelectric displacement sensor and the area-type photoelectric displacement sensor with the pressure control module 230 to apply the depress displacement in the Z-axis direction is almost the same. The only difference is that the linear-type photoelectric displacement sensor requires the user to touch the subject's wrist and mark the positions of Cun, Guan, and Chi with the largest amplitude on the wrist. In step S904B, the subject's wrist is placed at the measurement position, and the laser light emitted by the point-type photoelectric displacement sensor is aimed at the positions of the three marks. The detection position of the area-type photoelectric displacement sensor can be calculated because of its large detection area.

Please refer to FIG. 1 and FIGS. 9A-9B at the same time. FIGS. 9A-9B are flowcharts illustrating a method of using the pulse wave measuring device shown in FIG. 1 according to another embodiment of the present invention, wherein the pulse wave measuring device 100 does not have the scanning position control module 400, and the displacement sensing module 300 is a linear or area-type photoelectric displacement sensor, and the scanning position control module 400 has a Y-axis position controller. In the following, the radial artery of the wrist of the subject is taken as the test area 600 as an example for illustration.

In FIG. 9A, in step S902, the measurer touches the wrist of the subject and marks the point on the wrist where the amplitude is the largest to be the test area 600 of the subject. In step S904, the subject's wrist is placed at the measurement position, and the linear laser beam emitted by the linear photoelectric displacement sensor is aimed at the marked position, and the illuminated area of the linear laser beam is parallel to the X-axis.

Enter the aforementioned first stage of measurement. In step S906, the pressure control module 230 regulates the internal pressure of the airbag 200 to press the skin of the test subject in the Z-axis direction and adjusts to the initial pressure setting value (light pressure). In step S908, the pulse wave of the radial displacement of blood vessels at each position of the wrist along the area illuminated by the linear laser light is recorded.

In step 911, whether the end pressure set value is reached is checked.

If not, go to step S909, the amplitudes of the pulse wave at each position of the wrist are recorded. Then, go to step S910, the airbag 200 is adjusted by pressing down on the Z-axis to increase pressure, and then repeat step S908.

If yes, enter step S912. The gas valve of the airbag 200 is opened to release the pressure of the airbag 200. Then enter step S914, the X-axis coordinate positions where the maximum amplitudes occur and the corresponding pressures are compared to obtain the maximum amplitude positions of the Cun, Guan, and Chi of the subject.

Then, enter the second stage. Based on the maximum amplitude positions of Cun, Guan, and Chi of the subject obtained in step S914, enter steps S916 to S922 in FIG. 9B. After repeating the above steps S906 to S912 at the Cun, Guan, and Chi positions of the subject's wrist, enter step S924 to calculate the pulse-taking depth and depth ratio of the pulse wave.

Further, enter the third stage. In step S926, the depression depth of the airbag 200 in the Z-axis is adjusted to the pulse-taking depth. In step S928, whether the pulse-taking depth is reached is compared. If not, return to step S926 to adjust the depression depth of the airbag 200 in the Z axis to the pulse-taking depth. If yes, proceed to step S930 to capture pulse waves for a period of time (for example, 1 minute) and calculate pulse wave features.

What is claimed is:

1. A pulse wave measuring device for pulse diagnosis, configured to measure a vascular radial displacement pulse wave of an arterial blood vessel at a test area of a subject, the pulse wave measuring device comprising:

an airbag having a transparent window and a contact part, wherein the contact part is used to contact a skin of the test area of the subject to be tested, at least one arterial vessel is under the test area;

a pressure control module used to control an internal pressure of the airbag;

a displacement sensing module used to measure a real-time distance from the skin of the test area of the subject to the displacement sensing module over a period of time, so as to obtain the vascular radial displacement pulse wave of the arterial blood vessel, and wherein a measurement resolution of the displacement sensing module is below 50 μm; and a computer communicating with the pressure control module and the displacement sensing module respectively, used to transmit control signals to the pressure control module and the displacement sensing module respectively, receiving information sent by the pressure control module and the displacement sensing module, and performing calculations, wherein the computer is configured to process signals from the displacement sensing module to determine the vascular radial displacement pulse wave of the arterial blood vessel.

2. The device of claim 1, wherein the pressure control module comprises:

a pressure sensor for sensing the internal pressure of the airbag; and a pump for increasing or decreasing the internal pressure of the airbag.

3. The device of claim 1, wherein the displacement sensing module comprises a photoelectric displacement sensor configured to emit light through the transparent window of the airbag toward the contact part of the skin located under the contact part, and to receive reflected light so as to perform displacement measurement.

4. The device of claim 3, wherein the photoelectric displacement sensor comprises a distance measuring device of a laser displacement meter, a Fiber-Optic Sensor, a three-dimensional scanner, a time-of-flight distance measuring device, or a laser interferometer.

5. The device of claim 1, wherein the displacement sensing module further comprises a filter configured to filter out low-frequency respiratory signals of the subject so as to analyze pulse signals of the arterial blood vessel, or to filter out pulse signals of the arterial blood vessel so as to analyze a pressing depth of the airbag against the test area.

6. The device of claim 1, further comprising a scanning position control module, which is communicationally connected to the computer and used to control the position of the displacement sensing module in the test area to allow the displacement sensing module to perform distance-measurement scanning in the test area.

7. The device of claim 1, wherein computer is configured to:

(1) control the pressure control module to gradually increase the internal pressure of the airbag to an initial pressure value, and then control the pressure control module to maintain the internal pressure of the airbag at the initial pressure value, so that the displacement sensing module performs a first distance-measurement scan in the test area to obtain first measurement depths of respective points in the test area;

(2) control the pressure control module to gradually increase the internal pressure of the airbag to an end pressure value, and then control the pressure control module to maintain the internal pressure of the airbag at the end pressure value, so that the displacement sensing module performs a second distance-measurement scan in the test area to obtain second measurement depths of the respective points in the test area;

(3) find a location of an arterial blood vessel embedded in soft tissue by calculating differences between the first measurement depths and the second measurement depths of the respective points in the test area, wherein the arterial blood vessel is determined to be located at a point where the difference in depths is greater than that of adjacent points;

(4) control the pressure control module to gradually increase the internal pressure of the airbag from the initial pressure value to the end pressure value, while allowing the displacement sensing module to measure a radial displacement pulse wave of the arterial blood vessel, wherein when an amplitude of the radial displacement pulse wave is maximum, the internal pressure of the airbag is defined as a pulse-taking pressure, and a pressing depth of the airbag against the arterial blood vessel is defined as the pulse-taking depth; and (5) control the pressure control module to maintain the internal pressure of the airbag at the pulse-taking pressure to acquire a vascular radial displacement pulse waveform of the arterial blood vessel at the pulse-taking depth to obtain a pulse signal of the arterial blood vessel for pulse diagnosis.

8. A method for performing pulse diagnosis of a subject using the device of claim 1, the method comprising:

(1) placing the airbag of the device against the skin of the test area of the subject, the test area being located above an arterial blood vessel;

(2) controlling, by the computer, the pressure control module to gradually increase an internal pressure of the airbag to an initial pressure value and then maintain the internal pressure of the airbag at the initial pressure value, so that the displacement sensing module performs a first distance-measurement scan in the test area to obtain first measurement depths of the respective points in the test area;

(3) controlling, by the computer, the pressure control module to gradually increase the internal pressure of the airbag to an end pressure value and then maintain the internal pressure of the airbag at the end pressure value, so that the displacement sensing module performs a second distance-measurement scan in the test area to obtain second measurement depths of the respective points in the test area;

(4) determining, by the computer, a location of the arterial blood vessel embedded in soft tissue by calculating differences between the first measurement depths and the second measurement depths of the respective points in the test area, wherein the arterial blood vessel is determined to be located at a point where the difference in depths is greater than that of adjacent points;

(5) controlling, by the computer, the pressure control module to gradually increase the internal pressure of the airbag from the initial pressure value to the end pressure value, while allowing the displacement sensing module to measure a vascular radial displacement pulse wave of the arterial blood vessel, wherein when an amplitude of the vascular radial displacement pulse wave is maximum, the internal pressure of the airbag is defined as a pulse-taking pressure and a pressing depth of the airbag against the arterial blood vessel is defined as a pulse-taking depth; and (6) controlling, by the computer, the pressure control module to maintain the internal pressure of the airbag at the pulse-taking pressure to acquire a vascular radial displacement pulse waveform of the arterial blood vessel at the pulse-taking depth, thereby obtaining a pulse signal of the arterial blood vessel for pulse diagnosis.

9. The method of claim 8, wherein the step of controlling the internal pressure of the airbag comprises:

sensing the internal pressure of the airbag by a pressure sensor; and adjusting the internal pressure of the airbag by a pump to increase or decrease the internal pressure of the airbag.

10. The method of claim 8, wherein the step of measuring the distance by the displacement sensing module comprises emitting light from a photoelectric displacement sensor through the transparent window of the airbag toward the contact part or the skin located under the contact part, and receiving reflected light by the photoelectric displacement sensor so as to perform displacement measurement.

11. The method of claim 10, wherein the photoelectric displacement sensor comprises a distance measuring device of a laser displacement meter, a Fiber-Optic Sensor, a three-dimensional scanner, a time-of-flight distance measuring device, or a laser interferometer.

12. The method of claim 8, wherein the step of acquiring the vascular radial displacement pulse waveform comprises filtering, by a filter of the displacement sensing module, low-frequency respiratory signals of the subject so as to analyze pulse signals of the arterial blood vessel.

13. The method of claim 8, wherein the step of determining a pressing depth of the airbag comprises filtering, by a filter of the displacement sensing module, pulse signals of the arterial blood vessel so as to analyze a pressing depth of the airbag against the test area.

14. The method of claim 8, wherein the step of measuring the distance comprises automatically moving the displacement sensing module by a scanning position control module communicationally connected to the computer so as to perform distance-measurement scanning in the test area.

* * * * *